United States Patent [19]

Rousseau

[11] Patent Number: 5,491,408
[45] Date of Patent: Feb. 13, 1996

[54] DEVICE FOR DETECTING THE CHANGE OF VISCOSITY OF A LIQUID ELECTROLYTE BY DEPOLARIZATION EFFECT

[75] Inventor: Alain Rousseau, Charenton le Pont, France

[73] Assignee: Serbio, France

[21] Appl. No.: 732,362

[22] Filed: Jul. 18, 1991

[30] Foreign Application Priority Data

Jul. 20, 1990 [FR] France .................... 90 09285

[51] Int. Cl.$^6$ ................................ G01R 27/26
[52] U.S. Cl. .......................... 324/71.1; 128/637
[58] Field of Search ................... 324/71.1, 425, 324/439, 446; 204/222, 400; 73/54.41, 64.42; 128/632, 635, 637

[56] References Cited

U.S. PATENT DOCUMENTS

| | | | |
|---|---|---|---|
| 2,071,697 | 2/1957 | Larrabee | 324/425 |
| 2,878,106 | 3/1959 | Malmstadt | 324/439 |
| 2,989,377 | 6/1961 | Leisey | 324/439 |
| 3,134,728 | 5/1964 | Goldsmith | 204/400 |
| 3,267,364 | 8/1966 | Page et al. | 324/71.1 |
| 3,268,804 | 8/1966 | Young | 324/71.1 |
| 3,305,468 | 2/1967 | Liesch | 324/439 |
| 3,360,451 | 12/1967 | Stack, Jr. | 204/415 |
| 3,445,364 | 5/1969 | Strickler | 204/405 |
| 3,674,012 | 7/1972 | Sage | 128/637 |
| 3,999,538 | 12/1976 | Philpot, Jr. | 128/637 |
| 4,229,276 | 10/1980 | Kobayashi et al. | 204/222 |
| 4,558,589 | 12/1985 | Hemmes | 73/64.42 |
| 4,591,793 | 5/1986 | Freilich | 324/446 |
| 4,679,439 | 7/1987 | Culkin | 324/71.1 |
| 4,884,577 | 12/1989 | Merrill | 128/637 |
| 4,941,346 | 7/1990 | Suzuki et al. | 73/54.41 |
| 5,222,497 | 6/1993 | Ono | 128/637 |

FOREIGN PATENT DOCUMENTS

| | | | |
|---|---|---|---|
| 0007128 | 12/1987 | Japan | 128/637 |
| 0003240 | 1/1988 | Japan | 73/54.41 |
| 0904713 | 2/1982 | U.S.S.R. | 128/637 |
| 1120271 | 10/1984 | U.S.S.R. | 73/54.41 |
| 1242761 | 7/1986 | U.S.S.R. | 73/54.41 |
| 1449870 | 1/1989 | U.S.S.R. | 73/54.41 |

OTHER PUBLICATIONS

Medical and Biological Engineering Sep. 1976 Walker et al. Measurement of Blood Viscosity Using a Conicylindrical Viscometer.

*Primary Examiner*—Maura K. Regan
*Attorney, Agent, or Firm*—William A. Drucker

[57] ABSTRACT

A device is for measuring the coagulation time of a blood sample placed in contact with an appropriate reagent is described. A vibratory field inside an insulating receptacle is generated. Voltage variations between two electrodes disposed in the receptacle are measured which are indicative of a change in viscosity of the sample.

12 Claims, 2 Drawing Sheets

DEVICE FOR DETECTING THE CHANGE OF VISCOSITY OF A LIQUID ELECTROLYTE BY DEPOLARIZATION EFFECT

BACKGROUND OF THE INVENTION

The present invention relates to a device for detecting the change of viscosity of a fluid having the properties of an electrolyte.

More particularly, it is designed to measure the coagulation rate of a blood sample placed in contact with an appropriate reagent.

Numerous solutions have been proposed for measuring the rate of coagulation of blood such, for example, as the introduction of a ferromagnetic ball into the bottom of a cup containing the fluid to be tested, and which is driven with a periodic movement under the effect of an external magnetic field and in which the modifications of the movements of this ball, due to the modification of the physical state of said fluid, are detected.

These devices require the use of centrifuged blood or plasma introduced in an appreciable amount in a cup. Furthermore, the reagents used are lyophilized and must be reconstituted by means of distilled water at the time of their use.

The purpose of the present invention is to overcome this drawback by providing a device of simplified use permitting, on the one hand, ambulatory use for the personal use of patients under supervision who must carry out frequent tests, without using complicated, cumbersome equipment requiring sterilization after use and, on the other hand, making possible integrated tests which may contribute to the total automation in the conducting of analyses: (without reconstitution of the reagent, without conservation problems, etc. . . . )

For this, the invention is based on the depolarizing effect of the electrodes in an electrochemical cell which results from agitation of the electrolyte.

This effect has been ascertained by the Applicant, who has discovered that the voltage at the terminals of such a cell, when it is operating, begins by following a law of evolution characteristic of the polarization phenomenon and then levels out, which means that agitation of the electrolyte has had a depolarizing effect.

The Applicant then discovered that by using, as electrolyte, blood or plasma placed in the presence of a reagent which causes coagulation thereof after a certain time, the levelling out was itself followed by resumption of the normal law of evolution of the polarization curve.

Tests have shown that passing from the level portion to resumption of the normal law was critical and coincided with the instant of coagulation, such as it was determined by a traditional method.

The phenomenon will be the same whenever a liquid electrolyte undergoes a critical variation of its viscosity which will cause it to cease its agitation.

Furthermore, one of the difficulties of chronometric measurements is in being able to detect the zero instant when the plasma or the blood is placed in contact with the reagent. This device gives it straight off since, as soon as the electrolyte is introduced, the battery then formed delivers current which indicates very precisely the time t =0.

SUMMARY OF THE INVENTION

The invention then provides a device for detecting the change of viscosity of a fluid having the properties of an electrolyte, which is characterized in that it comprises: an electrically insulating receptacle with two electrodes (two different metals (e.g. copper and aluminium having a usable electrochemical couple)); means for generating a vibratory field inside the receptacle and means for detecting the variation of the potential of the electrodes which occurs after a certain time after introduction of the fluid into the receptacle, when said change takes place.

Such a device for measuring the coagulation time of a blood sample, placed in contact with an appropriate reagent, is also characterized in that said reagent is deposited in the form of a uniform layer on surfaces bathed by the electrolyte (formed for example by blood or plasma).

According to another characteristic of the invention, a disposable assembly intended to be used as element of the apparatus comprises a plastic material receptacle and two electrodes, adapted for cooperating removably with the means for generating a vibratory field and the means for detecting the variation of the potential of the electrodes, feeding into a given electric resistance.

According to another characteristic of the invention, the device comprises a flat insulating support on which are printed two electric circuits forming the conducting electrodes, these electrodes being interdigitated so as to form therebetween an insulating space serving as receptacle for a drop of blood.

BRIEF DESCRIPTION OF THE DRAWINGS

The invention will be further illustrated, by way of example, by the following description with reference to the accompanying drawings in which.

DESCRIPTION OF THE PREFERRED EMBODIMENT

Figure 1:
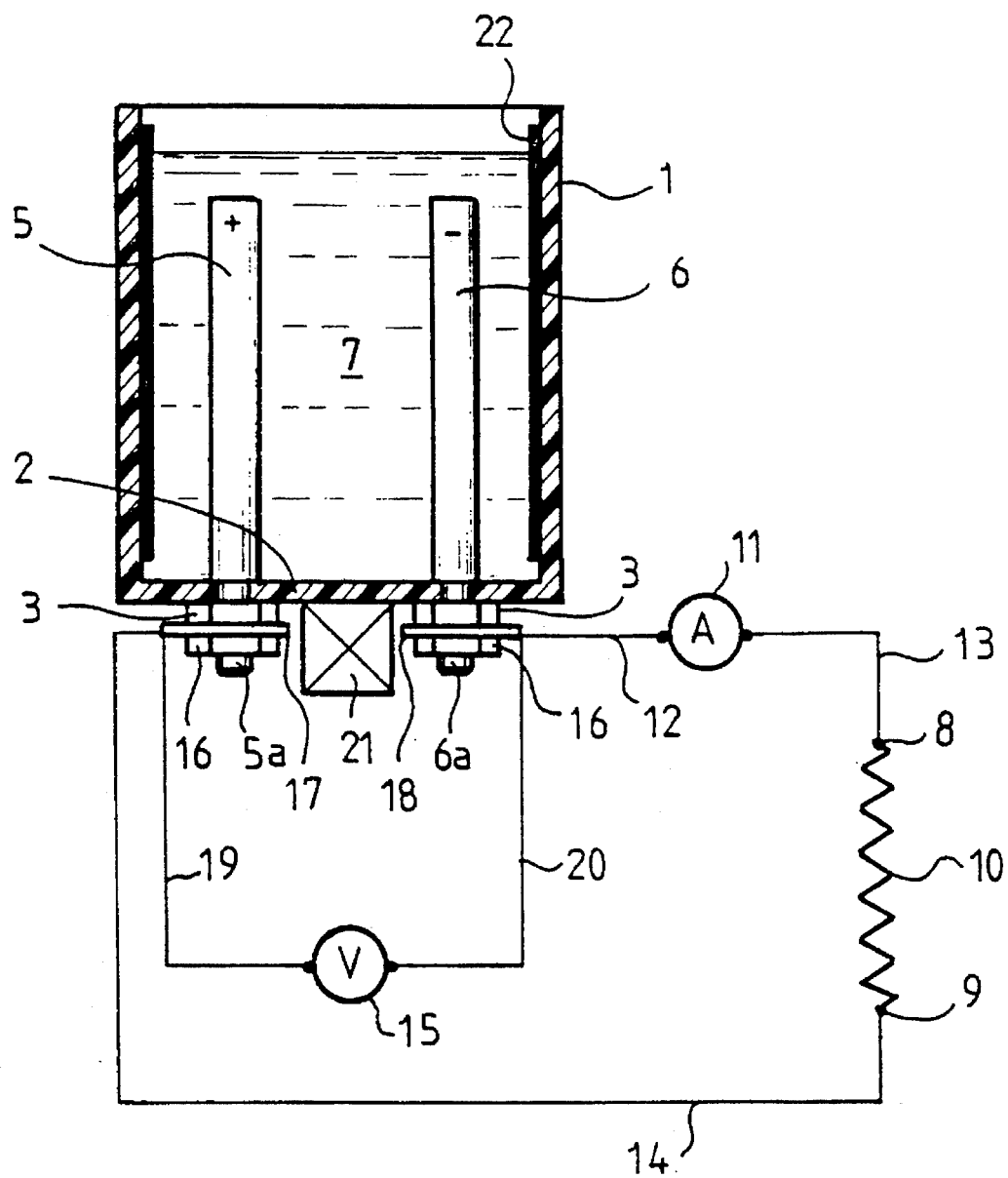
FIG. 1 is a schematic sectional view of a device for measuring the coagulation rate of blood in accordance with the invention.

The device shown in FIG. 1 is formed essentially of a tubular electrochemical cell 1 closed at its lower part by a bottom 2. Cell 1, made from an insulating material, supports an anode 5 and a cathode 6 fixed to the bottom 2, by two nuts 3 engaged with threaded ends 5a, 6a integral with electrodes 5, 6. Means, not shown, for passing sealingly through bottom 2 are provided.

This cell forms an electricity generator when an electrolyte is introduced therein, which will here be formed by blood whose coagulation time it is desired to measure.

Electrodes 5, 6 are connected electrically to terminals 8 and 9 of a load resistance 10 by means of an ammeter 11 disposed in series with resistance 10 by a circuit of conducting wires 12, 13, 14. The electrodes 5, 6 are further connected to a recording voltmeter 15 connected in parallel by wires 19, 20 across the ends 5a, 6a of electrodes 5, 6 thus forming connection terminals on which two lock nuts 16 are screwed, clamping two metal tags 17, 18 disposed at the ends respectively of wires 14, 19 and wires 12, 20.

A reagent 22, for causing the coagulation, is deposited on the lateral wall of cell 1 with a constant surface density. Preferably, the reagent is mixed with a gel which is then dried. This facilitates spreading it on the support concerned.

Thus formed, the device constitutes a disposable assembly to be used as element of the apparatus.

A vibration generator 21 is coupled for example to the bottom 2 of cell 1.

These vibrations may be provided by a piezoelectric generator generating acoustic vibrations having a frequency of a few hundred Hertz or else they may be generated by a vibrating table on which receptacle 1 is placed.

The apparatus operates in the following way.

At the time of introducing blood, the cell begins to feed into resistance 10 and, simultaneously, the vibration generator 21 is brought into service so as to cause agitation of the blood.

Simultaneously, the evolution of the voltage at the terminals 5a, 6a of cell 1 is recorded for a time going from the introduction of blood 7, closing the circuit and initializing the beginning of the measurement, until the moment when the artificially restrained voltage drop resumes once more its normal polarization curve, which time corresponds to that of the change of state of the blood, in fact to its coagulation.

Figure 2:
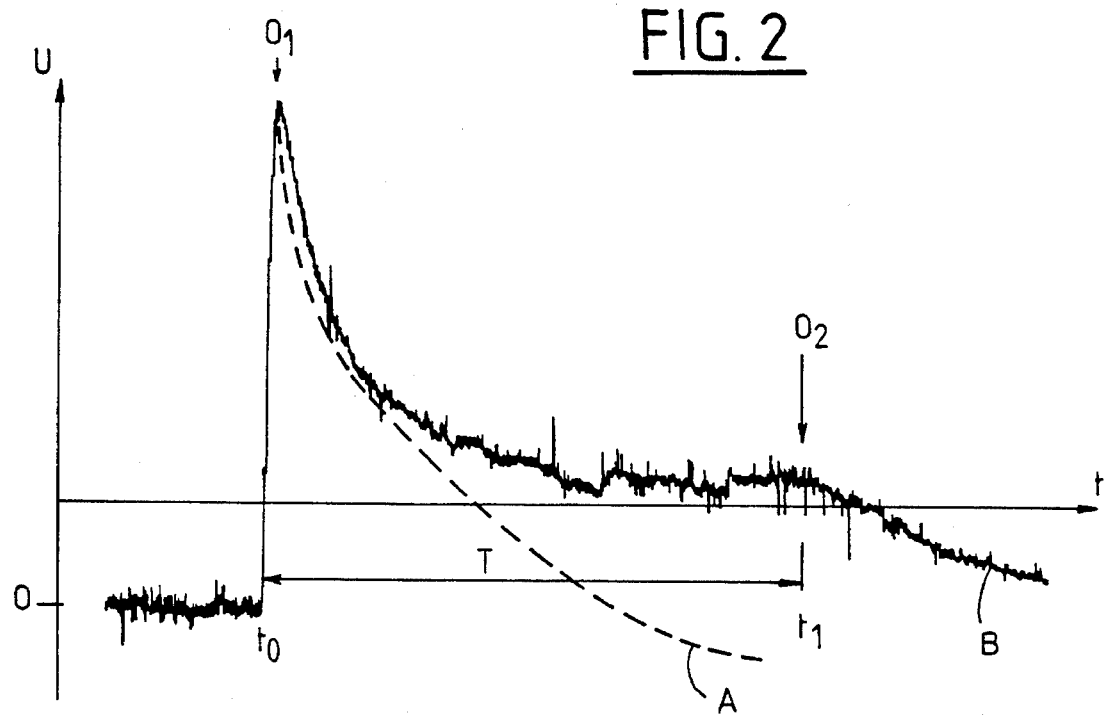
FIG. 2 is a curve illustrating the phenomenon put to use by the invention.

The curve of FIG. 2 illustrates perfectly the phenomenon of restraining the polarization when blood 7 is subjected to vibrations.

The fictitious curve A shows a known polarization curve, whereas curve B shows a curve obtained concretely when a vibrating phenomenon occurs. In both cases, it is a question of measuring the evolution of a voltage U as a function of a time t.

The beginning of polarization corresponds to point $O_1$ when blood 7 is introduced into cell 1 of the apparatus at a time $t_0$. The comparison of curves A and B clearly shows the restraining of the polarization (curve B) when the blood is subjected to vibrations as far as point $O_2$ corresponding to the point $t_1$ from which, blood 7 being entirely coagulated, the polarization curve B resumes its normal course.

The time T, equal to the difference between $t_0$ and $t_1$, corresponds to the coagulation time of the blood to be tested.

The operator may read this time directly from the recording.

By way of variation, it may be measured by signal processing devices associated with an electronic counting means, which will not be described here.

An essential advantage resides in the fact that the time measured is independent of the volume of liquid.

Figure 3:
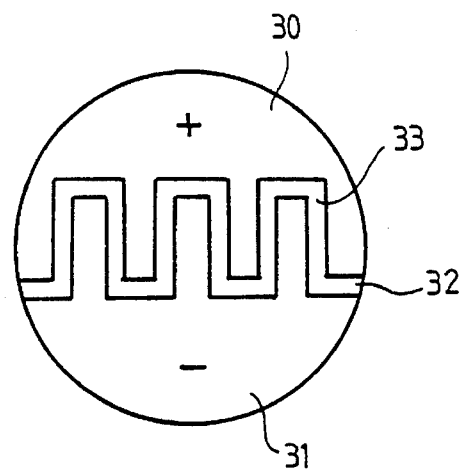
FIG. 3 is a schematic view of a particular embodiment of the electrodes of the device according to the invention.

The example shown in FIG. 3 corresponds to the same principle described above; it only differs from the preceding embodiment in that it is formed of positive and negative conducting electrodes 30, 31 obtained by photoprinting on a flat insulating medium 32. The printed circuits forming electrodes 30, 31 are interdigitated and form therebetween an insulating space 33. With such an arrangement, it is not only possible to have a considerable developed circuit length in a small given area but also is independent of the volume of blood used, a simple drop being sufficient to cover at least a part of the circuits thus formed. As before, it is the contact of the blood between the two electrodes 30,31 which initializes the measurement.

In addition, the reagent (not shown in this example) is deposited at least on one of the electrodes 30, 31, but for a better homogeneity of the coagulation, it is deposited on both.

Advantageously, the printed circuit is obtained on the bottom of cell 1 such as described above, the connecting and electric measurement device being unchanged.

What is claimed is:

1. Device for detecting coagulation of a blood sample, comprising: an electrically insulating receptacle with two conducting electrodes of different metallic nature; means for generating a vibratory field inside the receptacle; means for measuring voltage variations between the electrodes, and for recording in the form of a curve said voltage variations as a function of a time; and at least one appropriate reagent deposited in at least a uniform layer on surfaces of the receptacle bathed by the blood sample for causing said coagulation.

2. The device as claimed in claim 1, wherein said means for measuring voltage variations comprise a closed circuit connecting the electrodes to a resistance for causing polarization thereof.

3. The device as claimed in claim 1, wherein said means for measuring the voltage variations comprise means for recording said variations in order to determine a time of formation of a voltage between the electrodes when said blood sample is introduced into the receptacle and a time when the voltage undergoes a significant variation, characteristic of the coagulation.

4. The device as claimed in claim 1, wherein said receptacle is formed by a disposable assembly made of plastic material which comprises said two electrodes and which is removably assembled with the means for generating a vibratory field and the means for detecting said voltage variations.

5. The device as claimed in claim 1, wherein said means for generating a vibratory field are formed by a piezoelectric generator producing acoustic vibrations having frequency of a few hundred Hertz.

6. The device as claimed in claim 1, wherein said reagent is deposited prior to the introduction of the blood sample, in the form of at least one respective uniform layer on surfaces of said receptacle bathed by the blood sample.

7. Device for detecting coagulation of a blood drop comprising: a horizontal flat insulating support having an upper face for receiving a blood drop and on which are printed two electric circuits forming two conducting electrodes of different metallic nature, these electrodes being interdigitated so as to form therebetween an insulating space, said device further comprising means for measuring voltage variations between the electrodes, and for recording in the form of a curve said voltage variations as a function of a time; and at least one appropriate reagent deposited in at least one uniform layer on said support for causing said coagulation.

8. The device as claimed in claim 7, wherein at least one of said two electrodes constitutes a support for said at least one reagent.

9. The device as claimed in claim 7, wherein said means for measuring voltage variations comprise a closed circuit connecting the electrodes to a resistance for causing polarization thereof.

10. The device as claimed in claim 7, wherein said means for generating a vibratory field are formed by a piezoelectric generator producing acoustic vibrations having frequency of a few hundred Hertz.

11. A method for detecting a change of viscosity of a fluid sample having the properties of an electrolyte, said method comprising:

introducing the fluid sample into an electrically insulating receptacle having two electrodes of different metallic natures, simultaneously generating a vibratory field inside the fluid sample in the receptacle, simultaneously measuring voltage variations between said electrodes bathed by said fluid sample, and recording in the form of a curve said voltage variations as a function of a time, said curve comprising a first portion which reveals a restraining of polarization and a second portion which is joined to said first portion by a junction point and which resumes a normal course, and detecting on said curve said junction point, this point corresponding to a time when said change of viscosity occurred.

12. A method for measuring coagulation time of a blood sample, comprising:

introducing the blood sample into an electrically insulating receptacle having two electrodes of different metallic nature, placing said blood sample in contact with at least one reagent, simultaneously generating a vibratory field inside the blood sample in the receptacle, simultaneously measuring voltage variations between said electrodes bathed by said blood sample, and recording in the form of a curve said voltage variations as a function of a time, said curve comprising a first portion which reveals a restraining of polarization and a second portion which is joined to said first portion by a junction point and which resumes a normal course, detecting on said curve said junction point, this point corresponding to a determined time from which said blood sample is entirely coagulated, and measuring the coagulation time of said blood sample by counting a time interval between the introduction of said blood sample into the receptacle and said determined time.

* * * * *